United States Patent [19]

Tuseth

[11] Patent Number: 4,697,785
[45] Date of Patent: Oct. 6, 1987

[54] CLAMP FOR REGULATING FLOW OF PARENTERAL SOLUTIONS

[76] Inventor: Robert D. Tuseth, 10642 El Toro Ave., Fountain Valley, Calif. 92708

[21] Appl. No.: 851,462

[22] Filed: Apr. 14, 1986

[51] Int. Cl.⁴ .......................... F16L 55/14; F16K 7/06
[52] U.S. Cl. ......................................... 251/9; 137/595; 251/10; 251/251; 604/34; 604/250
[58] Field of Search ...................... 137/636, 636.1, 595, 137/863; 251/4, 6, 7, 9, 10, 251; 604/34, 250

[56] References Cited

U.S. PATENT DOCUMENTS

| Re. 31,584 | 5/1984 | Adelberg | 251/6 |
| 2,595,511 | 5/1952 | Butler | 251/6 |
| 3,016,915 | 1/1962 | Moeller, Jr. | 251/6 |
| 3,733,046 | 5/1973 | Press | 251/4 |
| 3,915,152 | 10/1975 | Colonna | 604/34 |
| 3,918,675 | 11/1975 | Forberg | 251/4 |
| 3,960,149 | 6/1976 | Bujan | 251/6 |
| 4,034,773 | 7/1977 | Huggins | 251/9 |
| 4,177,969 | 12/1979 | Seiber-Müller | 251/4 |
| 4,272,051 | 6/1981 | Huggins | 251/6 |

Primary Examiner—George L. Walton
Attorney, Agent, or Firm—Jackson & Jones

[57] ABSTRACT

A clamp for regulating the flow of parenteral solutions is disclosed which includes a clamp body having a channel for accommodating a length of administration set tubing so that a portion of the tubing is compressed to a closed position while at least one side of the tubing is left uncompressed to provide a passageway for the solution. A cam member or platen is moveably mounted on the clamp body for applying an adjustable compressive force against the uncompressed side of the tubing to vary the area of the passageway and the rate of flow of the solution.

14 Claims, 11 Drawing Figures

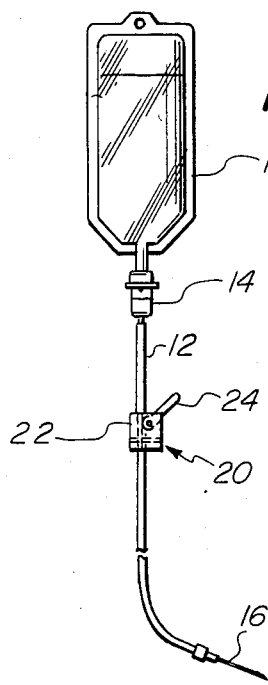
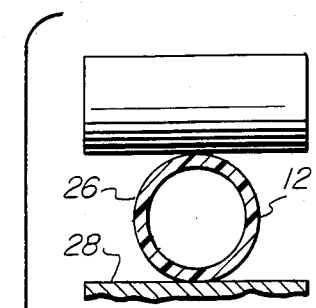
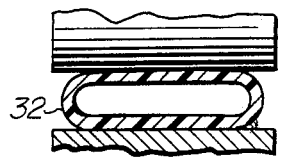
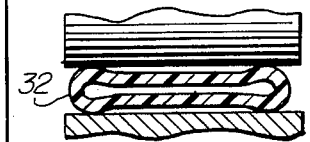
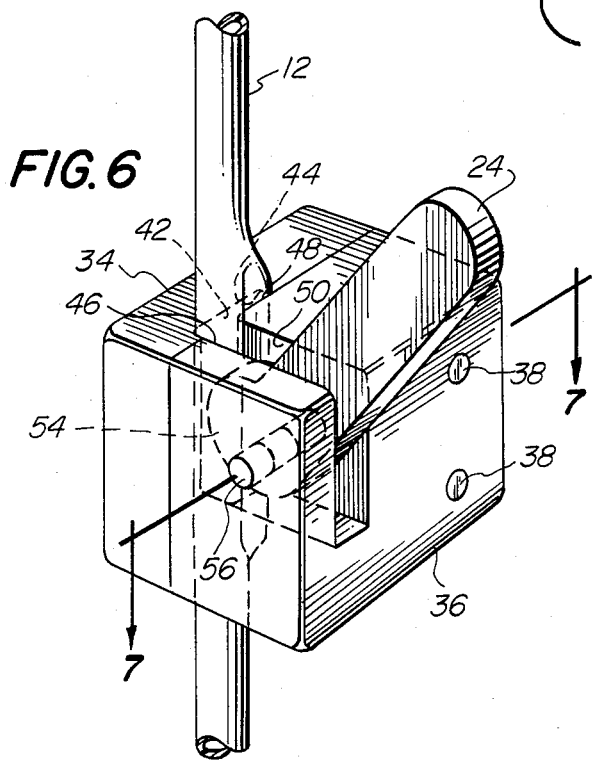
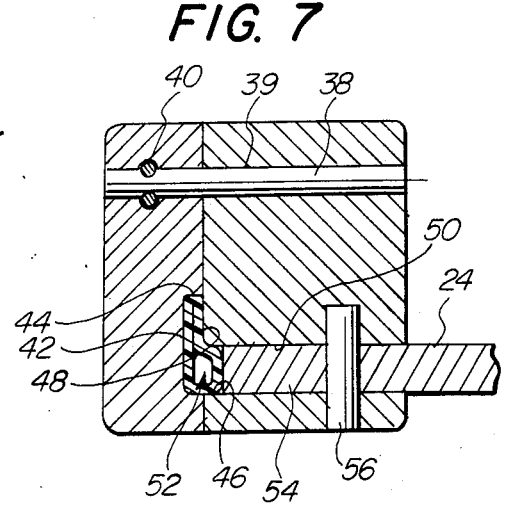

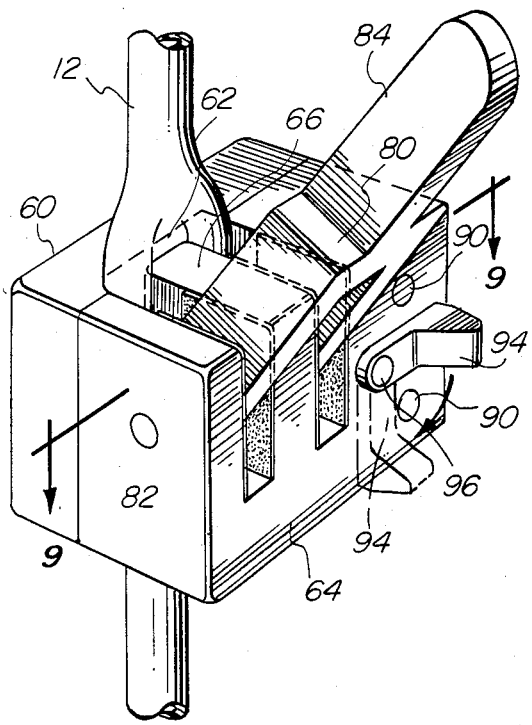
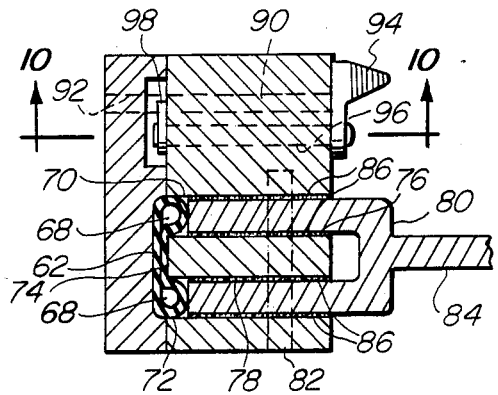
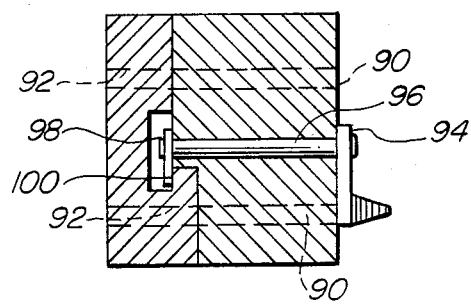
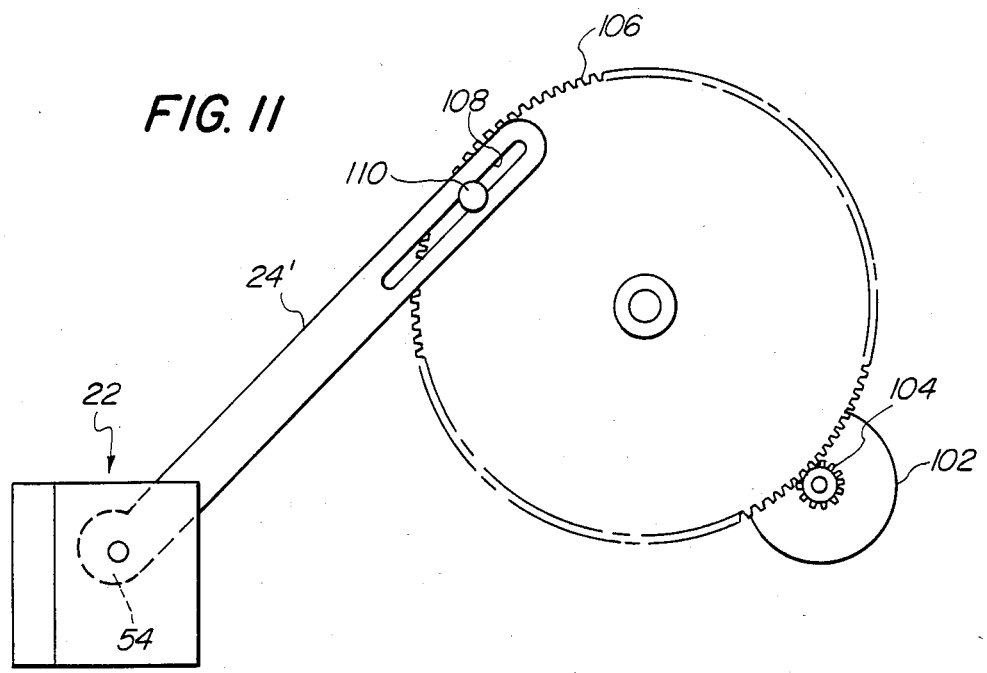

CLAMP FOR REGULATING FLOW OF PARENTERAL SOLUTIONS

FIELD OF THE INVENTION

This invention relates to parenteral solution equipment and, more particularly, to a clamp for regulating the fluid flow through such equipment.

BACKGROUND OF THE INVENTION

Parenteral solutions such as glucose, blood, etc. are conventionally provided in glass or flexible plastic bag containers. Such containers are normally supported in an inverted position for gravity discharge into a receiving body such as a patient. The container is connected to the patient by means of an administration set, i.e. a length of flexible tubing and a needle. The assimilation of the parenteral solution or fluid into the patient's body is slow and varies with the particular fluid. For this reason the flow rate must be closely regulated.

In the past, the flow rate of parenteral fluid has been regulated by pinching the tubing with a clamping device such as a roller clamp. See, for example, U.S. Pat. Nos. 2,595,511; 3,960,149 and 3,094,429. Such prior art clamps vary the internal cross section, or lumens, of the tubing by squeezing the entire width of the tube between a support surface and a roller, or moveable plate. While these prior art clamps are adjustable, small movements of the roller or plate result in large changes in flow rates over the normal range utilized in dispensing parenteral solutions.

The disadvantages of the prior art parenteral fluid flow regulating devices have been overcome by the present invention in which relatively large movements in a control member are required to effect small changes in the flow rate.

SUMMARY OF THE INVENTION

In accordance with the present invention, a clamp body is provided with a channel for accomodating a length of administration set tubing. The clamp body further includes means for compressing to a substantially closed position a portion of the tubing, while allowing at least one side thereof to provide a passageway for the flow of fluid therethrough. Means such as a platen or cam member is moveably mounted on the clamp body for applying a regulated compressive force to said one side of the tubing to thereby control the area of the passageway and the rate of fluid flowing through the tubing.

The construction and operation of the invention will be apparent from the following description taken in conjunction with the accompanying drawings.

BRIEF DESCRIPTION OF THE DRAWINGS

FIG. 1 is an elevational view of an intraveneous ("IV") administration set including a manually operable tubing clamp in accordance with the invention;

FIG. 2 is a cross-sectional view of an IV tubing positioned in a conventional roller type clamp and showing the tubing in an uncompressed state;

FIG. 3 is a cross-sectional view of the tubing of FIG. 2 in which the roller clamp has partially compressed the tubing;

FIG. 4 is a cross-sectional view of the tubing of FIG. 2 in which the roller clamp has further compressed the tubing;

FIG. 5 is a cross-sectional view of the tubing of FIG. 2 in which the roller clamp has completely compressed the tubing;

FIG. 6 is an enlarged perspective view of the clamp of FIG. 1;

FIG. 7 is a cross-sectional view of the clamp of FIG. 6 taken along lines 6—6;

FIG. 8 is a perspective view of another embodiment of a tubing clamp in accordance with the invention;

FIG. 9 is a cross-sectional view of the clamp of FIG. 8 taken along lines 9—9;

FIG. 10 is a cross-sectional view of the clamp of FIG. 8 taken along lines 10—10 of FIG. 9; and FIG. 11 is a perspective view of the clamp of FIG. 6 in which the clamp control lever is adjusted by means of a motor and gear arrangement.

DESCRIPTION OF THE PREFERRED EMBODIMENT

Referring now to the drawings and more particularly to FIG. 1, a container 10 of the fluid to be dispensed is connected to a length of flexible tubing 12 through a conventional drip chamber 14. A needle 16 is connected to the other end of the tubing for insertion into the patient in a well known manner. A flow regulating device or adjustable tubing clamp 20 is fastened to the tubing. The clamp 20 includes a clamp body 22 which surrounds a section of the tubing and a control lever 24 for exerting an incremental compressive force on a portion of the tubing to control the size of the channel or lumen within the tubing, thereby controlling the rate at which fluid will flow from the container 10 through the needle 16 and into the patient (not shown) as will be described in more detail.

Referring now to FIGS. 2, 3, 4, and 5, there is illustrated a conventional prior art roller clamp compressing a portion of a flexible administration set tubing 12 in successively increasing degrees.

The roller clamp of FIGS. 2 through 5 is shown as including only a roller 26 and a support surface 28 between which the tubing is compressed. The mechanism for adjusting the position of the roller 26 relative to the support surface is not illustrated for the sake of simplicity. As is shown in FIGS. 3, 4 and 5, little movement of the roller 26 toward the support surface 28 results in a large change in the size of the opening or channel 32 within the tubing through which the solution passes. For example, the difference between the position of the roller 28 in FIGS. 4 and 5 is very slight while the change in the tubing channel 32 is relatively large. This change in the tubing channel depicted in FIGS. 4 and 5 is particularly significant since the standard tubing has a nominal internal diameter of 0.125 inches and the opening for conventional flow rates is of the order of a few thousands of an inch to less than twenty thousands. Such prior art clamps are satisfactory for making course adjustments in flow rate, but unsatsifactory for making fine adjustments. As a result it is difficult and time consuming or even impossible to obtain a precise flow rate with the prior art clamps, and such precise control is important in many applications.

Referring now to FIGS. 6 and 7, the adjustable tubing clamp of the present invention includes a two-piece clamp body 20 consisting of a bottom section 34 and a top section 36 which are secured together by pins 38. The pins 38 are slidably received within bores 39, and include split spring rings 40 located at the lower ends thereof. The split rings 60 are arranged to expand slightly within an annular recess 42 in the bores 39 to secure the sections 34 and 36 together.

The clamp body defines a channel for accommodating a length of the flexible tubing 12. The channel is formed by a bottom support surface 42, a pair of opposing side walls 44 and 46, a top surface 48 and a third intermediate wall 50, which intersects the top surface 48 and extends parallel to wall 46. The top surface 48 extends over a portion of the bottom support surface and compresses that portion of the tubing positioned between the top and support surfaces into a closed or substantially closed position while allowing the uncompressed portion of the tubing to form an open channel 52 for the flow of parenteral fluid or solution therethrough. A platen or cam member 54 is moveably (i.e. pivotably) mounted on the clamp body 20 by means of a pin 56. The cam member 54 includes an integrally formed lever 24 which causes the cam member to progressively (incrementally) compress the portion of the tubing extending between walls 46 and 50 when the lever is moved clockwise as illustrated in FIG. 6.

Since the cam member 54 compresses only one side of the tubing (and not the entire width thereof) the size of the internal channel 52 changes gradually with relatively large movements of the lever 24. As a result, the tubing clamp of FIGS. 6 and 7 enables a fine and precise adjustment of the flow rate to be made.

Referring now to FIGS. 8 and 9, there is illustrated an alternative embodiment of my tubing clamp particularly adopted for use where relatively high flow rates are desired. In this embodiment, the lower clamp body section 60 defines a U-shaped channel with a bottom support surface 62. The upper clamp body section 64 includes a downwardly projecting portion 64 which extends over and compresses the central portion of the tubing 12 into a closed position so that the two sides of the tubing form channels 68 and 69 (sometimes referred to as the passageway) to regulate the flow of fluid to the patient. As shown the clamp body defines opposing side walls 70 and 72 and a top surface 74 which is formed by the downwardly projecting portion 64. The projecting portion 64 also forms side walls 76 and 78 which are parallel with the walls 70 and 72.

The sides of the tubing extend between the walls 70, 76 and 72, 78 to form the channels 68 and 69. A bifurcated cam member 80 is pivotally mounted on the upper clamp body section 64 by pin 82 so that movement of the lever 84 will increase or decrease, in incremental steps, the compressive force on the sides of the tubing to progressively open or close the channels 68 and 69, and thereby regulate the flow of fluid through the flexible tubing 12.

Friction surfaces 86, formed on the walls 70, 72 76 and 78 of the clamp body, contact the cam member 80 and maintain the member in place once the lever 84 has been adjusted to the desired position.

Alignment pins 90 are carried by the upper clamp body section 64 and slid into bores 92 in the bottom clamp body section 60. A latching device consisting of a latch lever 94, a shaft 91 and a dog 98 secure the lower and upper clamp body sections together. As is illustrated more particularly in FIG. 10, the dog 98 engages surface 100 of the lower clamp section 60 when the lever is rotated in a clockwise position to secure the two sections together. A counterclockwise rotation of the lever 94 allows the cam sections to be separated.

FIG. 11 illustrates the use of a conventional electric stepper motor 102 and a pair of gears 104 and 106 for adjusting the position of the cam lever 24. In this embodiment, the cam lever 24 includes a slot 108 in the upper end thereof within which a pin 110 fastened to the gear 106 rides.

In operation, the two clamp body members of FIGS. 6 or 8 are separated and a length of the flexible tubing 12 is placed on the bottom support surface of the lower sections. The upper and lower sections of the clamp body are then joined so that one side or the center portion of the tubing is compressed to a closed (or substantially closed) position. The cam control leverl 24 or 84 is then adjusted until the desired flow rate of the parenteral solution is obtained.

There has thus been described a novel tubing clamp for precisely regulating the flow of fluid through a length of tubing, such as administration set tubing. As is apparent from the above discussion, numerous modifications and adaptations of the preferred embodiment may be made without departing from the scope and spirit of the invention. For example, a plate or flat platen may be forced against one (FIG. 6) or both sides (FIG. 8) of the tubing to compress the same and thereby control the flow rate, instead of the eccentric cam illustrated. It is to be understood that the scope of the invention is defined by the appended claims.

What is claimed is:

1. In a clamp for regulating the flow of fluid through a length of flexible tubing the combination which comprises:
   (a) a clamp body defining a surface for supporting the flexible tubing, opposing walls extending from the support surface for providing a passageway for the tubing, and a top surface extending above and overlying a portion of the support surface which extends between the walls for permanently compressing the portion of the tubing positioned between the top and support surfaces into a closed position while allowing the uncompressed portion of the tubing to form an open channel for the flow of fluid therethrough; and
   (b) platen means moveably mounted on the clamp body and arranged to exert an incremental compressive force on the portion of the tubing forming the open channel to thereby control the size of channel and regulate the flow of fluid therethrough, said permanently compressed tubing portion being independent of the movement of said platen means.

2. The tubing clamp of claim 1 wherein the top surface abuts one wall so that the side of the tubing remote from said one wall forms the open channel.

3. The tubing clamp of claim 1 wherein the top surface extends over the central portion of the tubing so that each side of the tubing forms an open channel.

4. The tubing clamp of claim 1, wherein the platen means comprises a cam member pivotably mounted on the clamp body, the cam member having a lever extending from the clamp body and a cam surface extending above the support surface for engaging the tubing, the distance between the cam surface and support surface and the size of the open channel being regulated by the position of the lever.

5. The tubing clamp of claim 4, wherein the top surface abuts one wall so that the side of the tubing remote from said one wall forms an open channel and wherein the cam surface engages the side of the tubing which forms the open channel.

6. The tubing clamp of claim 4, wherein the top surface extends over the central portion of the support surface so that each side of the tubing forms an open channel and wherein the cam surface engages each side of the tubing.

7. In a clamp for incrementally regulating the flow of fluid through a flexible tubing the combination which comprises:
   (a) a clamp body defining a channel for accomodating a length of the flexible tubing including means for permanently compressing to a substantially closed position a portion of the tubing while allowing at least one side of the tubing to provide a passageway for the flow of fluid therethrough; and
   (b) means moveably mounted on the clamp body for applying a regulated compressive force to said one side of the tubing to thereby control the area of the passageway and the rate of liquid flowing through the tubing, said permanently compressed tubing portion being independent of the movement of said movable means.

8. The clamp of claim 7 wherein the compressing means is arranged to compress the other side of the tubing.

9. The clamp of claim 7, wherein the compressing means is arranged to compress the center portion of the tubing while allowing both sides of the tubing to provide a passageway for the flow of fluid therethrough.

10. The clamp of claim 8, wherein the means moveably mounted on the clamp body is a platen which engages said one side of the tubing.

11. The clamp of claim 9, wherein the means moveably mounted on the clamp body is a platen which engages each side of the tubing.

12. The clamp of claim 7, wherein the clamp body defines an elongated channel having a bottom support surface a pair of opposing upstanding walls and a top surface extending over a portion of the bottom surface while allowing a portion of the tubing to extend between the top surface and at least wall, the compressing means comprising the top surface and the portion of the bottom surface extending below said top surface.

13. The clamp of claim 12, wherein the top surface extends from one wall to allow the side of the tubing remote from said one wall to provide a passageway for the flow of fluid.

14. The clamp of claim 12, wherein the top surface extends over the central portion of the bottom support surface to allow both sides of the tubing to provide a pasageway for the flow of fluid.

* * * * *